(12) United States Patent
Schenck

(10) Patent No.: US 8,555,888 B1
(45) Date of Patent: Oct. 15, 2013

(54) PRESSURE RELIEF GEL PADS

(75) Inventor: David Schenck, Erie, PA (US)

(73) Assignee: Trauma Technologies, Inc., Lake City, PA (US)

( * ) Notice: Subject to any disclaimer, the term of this patent is extended or adjusted under 35 U.S.C. 154(b) by 1686 days.

(21) Appl. No.: 11/715,101

(22) Filed: Mar. 7, 2007

(51) Int. Cl.
*A61G 15/00* (2006.01)
*A43B 13/20* (2006.01)

(52) U.S. Cl.
USPC .......................................... 128/845; 36/30 R

(58) Field of Classification Search
USPC .............. 128/845; 2/456, 463, 462, 411, 413, 2/414, 69, 92; 36/30 R
See application file for complete search history.

(56) References Cited

U.S. PATENT DOCUMENTS

| | | | | |
|---|---|---|---|---|
| 4,292,263 A * | 9/1981 | Hanrahan et al. | ............ | 264/46.9 |
| 4,910,978 A * | 3/1990 | Gordon et al. | .................. | 62/530 |
| 5,098,421 A * | 3/1992 | Zook | ............................. | 604/367 |
| 5,743,867 A * | 4/1998 | Hickling | ......................... | 602/65 |
| 6,810,603 B1 * | 11/2004 | Cosentino | ........................ | 36/8.3 |
| 7,445,608 B2 * | 11/2008 | Dunfee et al. | .................. | 602/19 |
| 2002/0157163 A1 * | 10/2002 | Chen | ................................. | 2/16 |
| 2005/0086838 A1 * | 4/2005 | Khantzis | ....................... | 36/30 R |
| 2007/0077860 A1 * | 4/2007 | Brooks | ......................... | 450/155 |
| 2008/0125842 A1 * | 5/2008 | Petitt | ............................. | 607/108 |

* cited by examiner

*Primary Examiner* — Patricia Bianco
*Assistant Examiner* — Tarla Patel
(74) *Attorney, Agent, or Firm* — Richard K. Thomson

(57) ABSTRACT

Support pads for reducing the pressure exerted on some portion of the human body are disclosed. A first transparent flexible plastic sheet is bonded to a layer of four-way stretchable polyamide fabric which houses a medical-grade gel. An external surface of the four-way stretchable fabric is coated with urethane to avoid migration of the enclosed gel. This support pad exerts a pressure that is below the level producing venous stasis (0.5 psi).

4 Claims, No Drawings

PRESSURE RELIEF GEL PADS

BACKGROUND AND SUMMARY OF THE INVENTION

The present invention is directed to the field of medical supplies. More particularly, the present invention is directed to pressure relief pads, or gel packs, for support of patients/users in a variety of applications, the gel packs reducing the pressure applied to the patient's body below a level to cause venous stasis.

An earlier patent belonging to applicant entitled "Backboard with Removable Pad" bearing U.S. Pat. No. 6,848,134 is hereby incorporated by reference. That patent is directed to a backboard for supporting/transporting patients to a ambulance, for example. The backboard of that invention utilized a number of gel packs to undergird the patient and enhance comfort. The problem with the gel packs used therein, and gel packs in general, is that they "push back" with too great a pressure and can cause venous stasis, a cutting off of the blood flow which can cause extremities to "go to sleep", or in case of prolonged contact, can cause ulcerations commonly known as "bed sores". The problem is most acute at the outer regions of the gel packs where a "hammock effect" increases pressure in the gel packs toward their outer edges.

The present invention is a pad for supporting at least a portion of a human body, the pad comprising: a) a compartment having at least a first body-contacting surface made of four-way stretchable fabric; b) a medical-grade gel contained within the compartment; whereby the medical-grade gel and the four-way stretchable fabric synergistically combine to provide a support exerting a pressure below that which causes venous stasis. Preferably, the four-way stretchable fabric is made of polyamide fabric, and more preferably, is made from elastane fibers. Elastane, also known as spandex, which has one side coated with polyurethane, is commercially available from Dartex Coatings identified as Dartex fabric. An external surface of the four-way stretchable fabric is coated with urethane to prevent migration of said medical-grade gel there through.

Various other features, advantages, and characteristics of the present invention will become apparent after a reading of the following detailed description.

DETAILED DESCRIPTION OF THE PREFERRED EMBODIMENT(S)

The support pad of the present invention comprises a compartment having a lower layer of durable, flexible plastic sheeting identical to the materials currently used in the gel pack industry. The medical-grade gels themselves can be any of those currently in use including the one disclosed in U.S. Pat. No. 6,848,134 sold under the trademark ISOGEL by Pittsburgh Plastics Manufacturing, Inc. of Butler, Pa. The gels used have Shore durometer hardnesses in the range of between 20 and 75. It will be understood, however, that the performance of this invention does not depend on the particular manufacturer of the gel, since gels manufactured by others have produced equally acceptable results. Indeed, the specifics of the durometer of the gel plays little or no role in the pressure reduction afforded by this invention.

The key element of the invention seems to lie in the use of a four-way stretchable material as the upper, or patient/user contacting surface. The material of choice is a polyamide fabric commonly identified as spandex or elastane, which is coated with urethane to prevent migration of the gel through the fabric. Somewhat counter-intuitively, the coating must be on the exterior surface of the pad. If the fabric is reversed, some inexplicable interaction between the gel and the coating significantly reduces the benefits of the invention. Further, with the coated side out, the material is protected against growth of fungi and bacteria. A specific fabric found to produce beneficial results is Dartex fabric available from Dartex Coatings. The product identification sheet from the manufacturer indicates that, by weight, the product is 49% polyamide fibers, 10% elastane, and 41% polyurethane coating. The ability of the fabric to stretch equally in every direction (referred to herein as four-way stretchability), in conjunction with the properties of the enclosed gel, synergistically combine to avoid the "hammock effect", a deficiency of existing gel packs, which causes a pressure build up toward the outer edges of the pack. This pressure buildup pressing back against a patient's body, causes venous stasis, a cutting off of the blood flow which can cause the limbs to "go to sleep" and, with extended contact, can result in creation of bed sores. The pressure which has been determined to cause venous stasis is 26 mm of Mercury (0.50 psi). Conventional gel pads exert a pressure of 32 mm of Mercury, or 0.62 psi. The gel pads of the present invention produce a 20% reduction in pressure or, a resultant pressure of less than 26 mm of Mercury (a pressure of 0.495 psi). As far as applicant is aware, the gel pads of the present invention are the only support pads of any sort capable of eliminating the problem of venous stasis. Indeed, a gel pad having ⅜" thickness produces superior pressure reduction to 6" of conventional open-cell foam. Further, as it relates to the backboard application of U.S. Pat. No. 6,848,134, the improved pressure relief available with the support pads of the present invention, has obviated the use of air bladders. Indeed, it has been found that the use of over-inflated air bladders can actually agitate a patient rather than enhance their comfort.

The applications for the pads of this invention are virtually boundless. Anywhere pressure reduction between an object or article and a portion of the human body is beneficial, the support pads of the present invention could be used. Pads used in prosthetic devices employing the features of the present invention would eliminate the creation of sores. Similarly, shoe inserts, particularly for diabetics where creation of sores can lead to the loss of one or more toes, would reduce this risk. Pads on x-ray tables, patient examination tables, plastic surgery tables could all benefit from the synergy of the gel enclosed in plastic and elastane. Other applications include pads for wheel chairs, race car seats, inserts for car seats. It will be understood that although ⅜" thickness of gel is adequate for most applications, the configuration of some wheel chairs require a pad having a thickness of 1", for example. Accordingly, the configuration of the car seats may necessitate a thicker pad. Knee pads for sports enthusiasts including football players, skateboarders, and roller skaters; elbow pads, helmet liners for all types of protective head gear; kneeling pads; airline seat pads; stadium cushions; pads on car dollys; wrestling and dancing mats; toilet bowl seats; therapeutic "donuts"; each of these applications would benefit from the pressure reduction available through the pads of the present invention.

Various changes, alternatives, and modifications will become apparent to a person of ordinary skill in the art after a reading of the foregoing specification. It is intended that all such changes, alternatives, and modifications as fall within the scope of the appended claims be considered part of the present invention.

I claim:

1. A pad for supporting at least a portion of a human body while a patient lies substantially motionless for a prolonged period of time, said pad producing a contact pressure of less than 0.495 psi and comprising:

a) a compartment having at least a first body-contacting surface made of a four-way stretchable fabric having elastane fibers incorporated therein;

b) a medical-grade gel contained within said compartment;

whereby said medical-grade gel and said four-way stretchable fabric synergistically combine to provide a support for the portion of the body while laying substantially motionless which exerts a pressure of less than 0.495 psi, below that which causes venous stasis.

2. The pad of claim 1 wherein said four-way stretchable fabric is made of polyamide fabric.

3. The pad of claim 2 wherein said four-way stretchable fabric is made of 10% elastane fibers.

4. The pad of claim 3 wherein an external surface of said four-way stretchable fabric is coated with urethane to prevent migration of said medical-grade gel there through.

\* \* \* \* \*